United States Patent [19]

Lonardo

[11] Patent Number: 4,848,326
[45] Date of Patent: Jul. 18, 1989

[54] KNEE CONTRACTURE CORRECTION DEVICE

[76] Inventor: Robert Lonardo, 680 Capri Blvd., Treasure Island, Fla. 33706

[21] Appl. No.: 209,012

[22] Filed: Jun. 20, 1988

[51] Int. Cl.$^4$ .............................................. A61F 3/00
[52] U.S. Cl. ................................ 128/80 F; 128/80 R
[58] Field of Search ................. 128/80 C, 80 E, 80 F, 128/80 J, 80 B, 80 R

[56] References Cited

U.S. PATENT DOCUMENTS

| | | | |
|---|---|---|---|
| 1,638,285 | 8/1927 | Brooks | 128/80 E |
| 2,512,826 | 6/1950 | Clark | 128/80 F |
| 2,516,253 | 7/1950 | Pieterick | 128/80 F |
| 2,545,843 | 3/1951 | Cohan | 128/80 F |
| 2,557,604 | 6/1951 | Invidiato | 128/80 F |
| 2,558,986 | 7/1951 | Seelert | 128/80 F |
| 2,573,866 | 11/1951 | Murphy | 128/80 F |
| 2,934,064 | 4/1960 | Invidiato | 128/80 F |
| 3,086,522 | 4/1963 | Frahmader | 128/80 J |
| 3,976,059 | 8/1976 | Lonardo | 128/80 E |

FOREIGN PATENT DOCUMENTS 536341  5/1941  United Kingdom ............. 128/80 F

OTHER PUBLICATIONS

Braces Today, Mar. 1950, 4 pages.

*Primary Examiner*—Edgar S. Burr
*Assistant Examiner*—Huong Q. Pham

[57] ABSTRACT

A knee contracture correction device for straightening a contracted knee is provided. The device includes a pair of rod assemblies each having opposite upper and lower ends and a pivotal joint between the ends. The upper end of the rod assemblies is pivotally secured to the patient's thigh while the lower end is pivotally secured adjacent the patient's ankle. The pivotal joint of the rod assemblies is locked so as to define an obtuse angle slightly greater than the angle of contracture of the knee. Straps are positioned immediately above and below the knee and fastened to the rod assemblies so as to stretch the knee ligaments and muscles. Periodically, the angle of the rod assemblies is increased until eventually the knee contracture is eliminated.

10 Claims, 8 Drawing Sheets

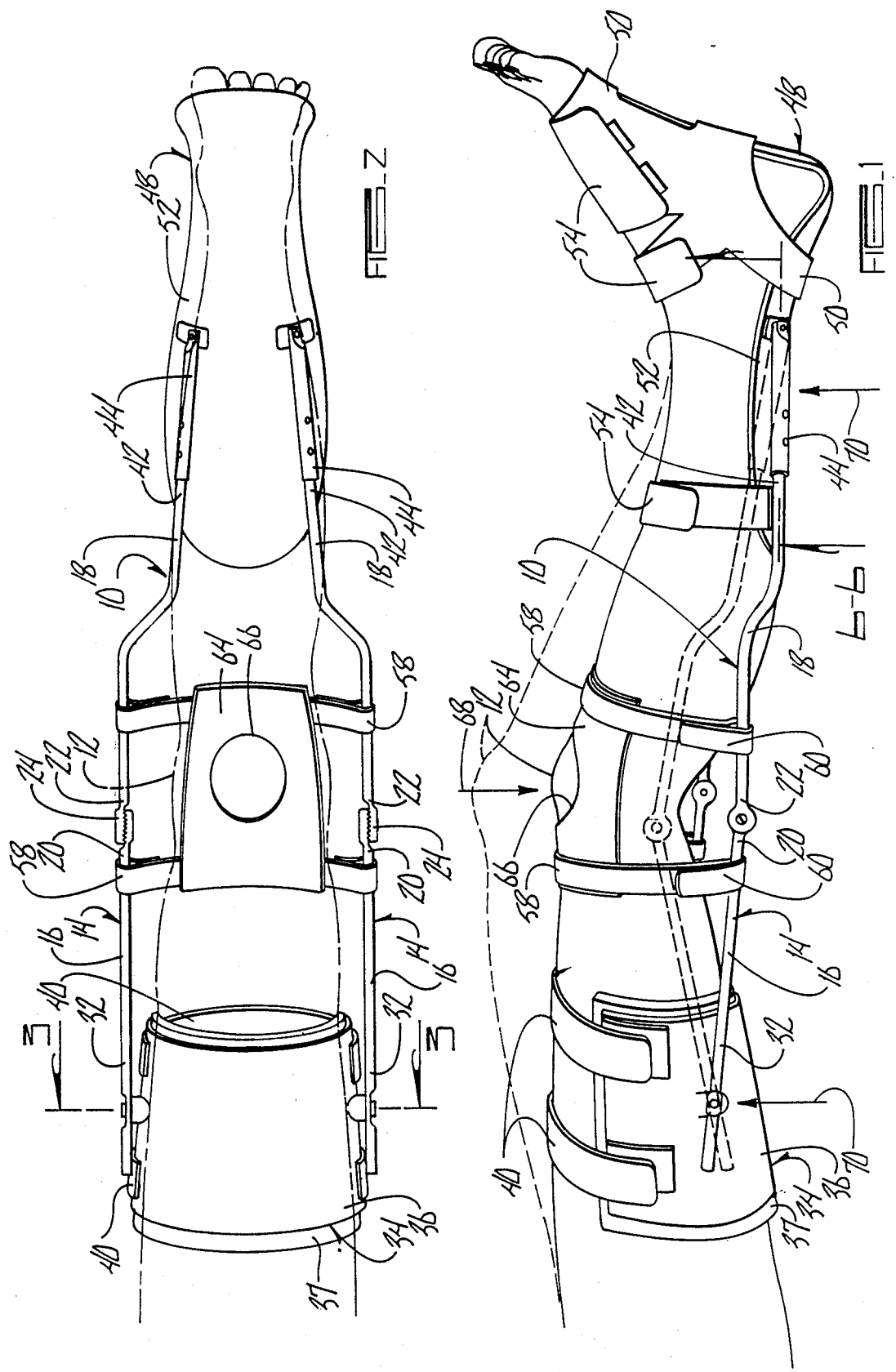

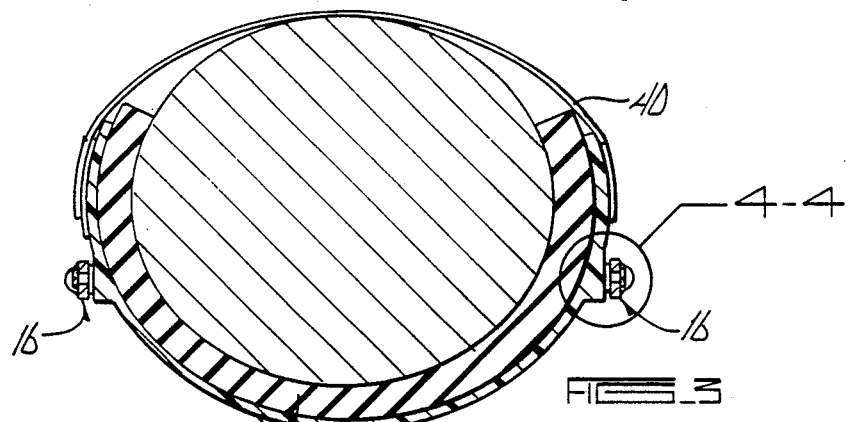
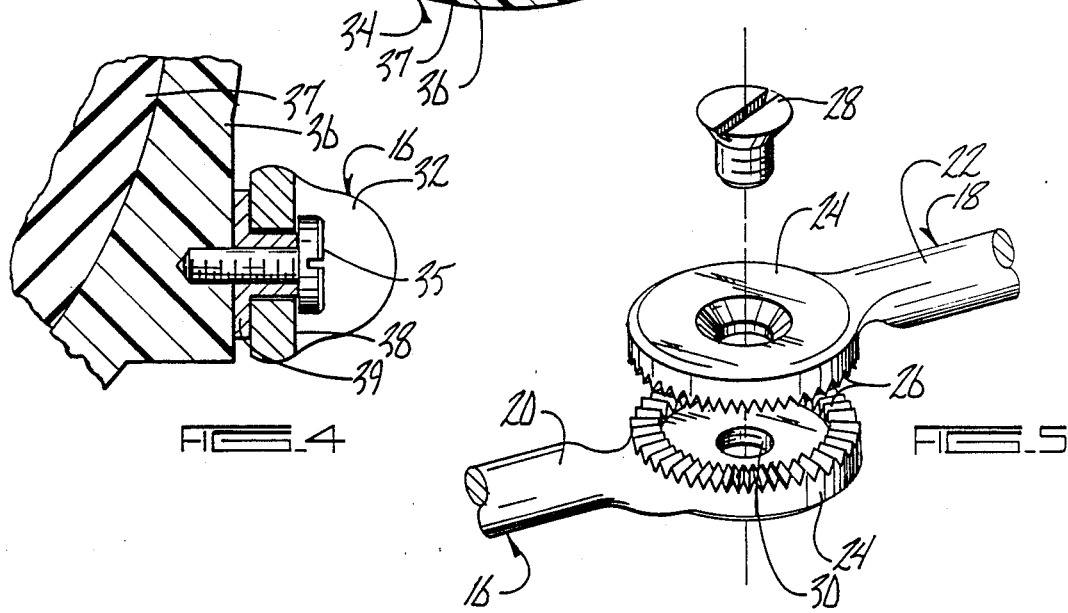
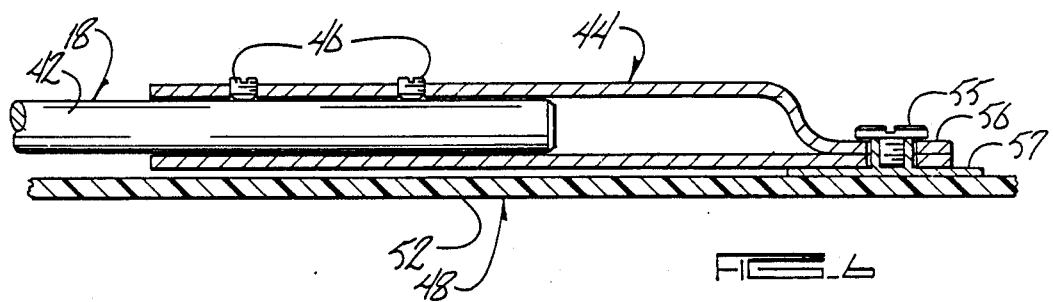

KNEE CONTRACTURE CORRECTION DEVICE

BACKGROUND OF THE INVENTION

When a patient has a paretic or painful disability and habitually sits or lies for prolonged periods with the knees flexed, knee contractures develop rapidly with progressive limitation of extension of the knees. If the knees are not stretched to full extension by standing and walking each day, tightness develops in the hamstring and gastrocnemius muscles and the posterior capsule of the joint, thereby causing flexion in the knees. The placing of pillows or other supports under the knees results in more rapid development of contractures.

For example, contractures are noticeable in patients who have been confined to bed for four days. By the end of ten days, the contractures are significant. After fourteen days, gross contractures or near crippling deformities are present. Recovery or correction of the contractures is a slow process. Each day after the fourteenth day in which the knees are not stretched will require then days to return the knee joint to a functional state, but less than a full range of movement. Recovery will also vary depending on the individual's condition and health.

Therefore, a primary objective of the present invention is the provision of a knee contracture correction device for use by any patient having knee contractures.

A further objective of the present invention is the provision of a knee contracture correction device which can be used by both mobile and immobile patients.

A further objective of the present invention is a device for correcting knee contractures for use by different persons having varying degrees of knee contractures and having varying dimensions of legs.

Yet another objective of the present invention is the provision of knee contraction correction device which is economical to manufacture, and which is durable, safe and easy to use.

These and other objectives will become apparent from the following description of the present invention.

SUMMARY OF THE INVENTION

The knee contracture correction device of the present invention is for use by patients who are confined to a bed or chair for prolonged periods with flexed knees. The device can be used in conjunction with a foot splint having a foot portion and a leg portion integrally formed at substantially right angles to one another, such as that described in applicant's previous U.S. Pat. No. 3,976,059 issued on Aug. 24, 1976. Such a foot splint can be used to correct contractures of the ankles which also occur in immobile people.

The brace of the present invention includes a pair of elongated rod assemblies positioned on opposite sides of the patient's leg and extending substantially along the length of the leg. The upper end of each rod assembly is pivotally secured to a thigh strap extending around the patient's thigh. The lower end of the rod assembly is pivotally and slidably secured to the leg portion of the foot splint. Each rod assembly has a pivot joint intermediate the opposite ends thereof and adjacent the patient's knee. A pair of tension straps secured to each rod assembly extends in front of the patient's leg immediately above and below the patient's knee, so as to pull the knee towards the pivotal joint of the rod assemblies and thereby stretch the knee ligaments and muscles.

In use, the knee contracture correction device is strapped to the patient's leg with the upper and lower rod sections being angled with respect to one another. The pivot joint of the rod assembly is tightened along with the leg straps such that the knee is stretched to an extent defined by the angle of the rod sections. Periodically, the angle between the upper and lower rod sections is increased so as to further stretch the knee, until contracture of the knee is eliminated.

A BRIEF DESCRIPTION OF THE DRAWINGS

FIG. 1 is a side elevation view showing the knee contracture correction device of the present invention in position on a patient's leg.

FIG. 2 is a top plan view of the device.

FIG. 3 is a sectional view taken along lines 3—3 of FIG. 2.

FIG. 4 is an enlarged view of the area within line 4—4 of FIG. 3.

FIG. 5 is an enlarged exploded perspective view showing the pivotal joint of a rod assembly.

FIG. 6 is a partial sectional view taken along lines 6—6 of FIG. 1.

DETAILED DESCRIPTION OF THE DRAWINGS

The knee contracture correction device or brace of the present invention is generally designated by the reference numeral 10 in the drawings. Device 10 is used to straighten the leg of a patient whose knee 12 has contracted as a result of immobility or other causes.

More particularly, device 10 includes a pair of elongated rod assemblies 14, each including an upper rod section 16 and a lower rod section 18. The lower end 20 of upper rod section 16 and the upper end 22 of lower rod section 18 each have an enlarged disc 24 having a plurality of serrations 26 extending around the perimeter thereof, as seen in FIG. 5. Lower end 20 of upper rod section 16 and upper end 22 of lower rod section 18 overlap one another such that serrations 26 on discs 24 matingly engage one another. Discs 24 are lockingly connected by screw 28 whose threads matingly engage a threaded aperture 30 in one of discs 24. Rod sections 16 and 18 can be set at any angle with respect to one another and screw 28 tightened so as to maintain the desired angle. Alternatively, a nut and bolt or any other conventional fastener can be used to lockingly secure the connected ends 20, 22 of rod sections 16, 18.

The upper end 32 of upper rod section 16 is pivotally attached to a thigh pad 34 by means of a screw 35, or the like. Thigh pad 34 includes a substantially rigid outer shell 36 lined with soft padding 37. The pad 34 should have a length measured along the leg of at least 4 inches so as to provide a substantial contact area in engagement with the leg to create an adequate anchor for the upper end of the apparatus. Screw 35 extends through a hole in a flattened portion 38 of end 32 of rod section 16, and into thigh pad shell 36. A pivot bearing 39 resides between shell 36 and rod section 16 and extends into the hole in the rod section, as best seen in FIG. 4. Thigh pad 34 is secured to the patient's thigh in any convenient manner, such as by Velcro straps 40.

The lower end 42 of lower rod section 18 is slidably received within a tube 44. Set screws 46 or the like maintain lower end 42 in the selected position within tube 44, as seen in FIG. 6.

Tube 44 is anchored to the patient's lower leg adjacent the ankle in any convenient means. Preferably the anchoring means is a foot splint 48 such as that described in applicant's prior U.S. Pat. No. 3,976,059 issued Aug. 24, 1976. Since foot and ankle contractures normally accompany knee contractures, it is logical to employ knee contracture correction device 10 in conjunction with foot splint 48 which can be used to correct the foot contracture. Foot splint 48 generally includes a foot portion 50 and a leg portion 52 which are integrally formed at substantially right angles to one another. Splint 48 is secured to the patient's lower leg and foot by Velcro straps 54. More particularly, a screw 55 or the like extends through a hole in a flattened portion 56 on end 42 of rod section 18, and into a pivot bearing 57 secured to leg portion 52 of splint 48.

In use, device 10 is strapped on the patient's leg via thigh pad 34 and foot splint 48. Preferably, straps 40 and 54 and no less than 8 inches from the patient's knee. The pivotal joint of rod assemblies 14 is adjusted so that the upper and lower rod sections are set at an obtuse angle with respect to one another. This obtuse angle is slightly greater than the angle of contracture of the knee. The initial position of the contractured knee and device 10 are shown by broken lines in FIG. 1. Lower end 42 of lower rod section 18 is fixed in position within tube 44 by set screws 46.

A pair of tension straps 58 are positioned above and below the knee and are fastened at opposite ends to rod assemblies 14 so as to stretch the ligaments and muscles attached to the patient's knee. Preferably, straps 58 have opposite ends 60 each of which are extends around one of the rod assemblies 14 and are secured by Velcro. Thus, tension straps 58 extend from one rod assembly to the other and are substantially U-shaped during use. Straps 58 may be interconnected by an elasticized material 64 having an opening 66 for the kneecap. Material 64 distributes the pulling forces of straps 58 over a broader surface area of the patient's knee.

As the knee stretches, the angle between upper and lower rod sections 16, 18 can be periodically increased so as to further stretch the knee ligaments and muscles, until the knee contracture is eventually eliminated. In the final phase of use, rod assemblies 14 will be substantially straight, as shown by solid lines in FIG. 1.

Thus, device or brace 10 of the present invention stretches the contracted knee by applying pressure at three locations on the patient's leg. More particularly, a first pressure as indicated by arrow 68 in FIG. 1 is exerted on the knee of the patient, while counter-pressures, represented by arrow 70 are exerted on the back of the patient's thigh and lower leg or calf. Preferably, the upper and lower ends of brace 10 are secured to the patient's leg as far as possible from the knee so as to maximize the leverage and counter-pressure acting to straighten the knee.

From the foregoing, it can be seen that the present invention accomplishes at least all of the stated objectives.

What is claimed is:

1. A knee contracture correction device for straightening a contracted knee, comprises:
    a pair of rod assemblies each having opposite upper and lower ends and a pivotal joint between the ends;
    first anchor means for pivotally securing the upper ends of the rod assemblies to a patient's thigh adjacent the upper ends thereof, with one rod assembly being positioned on each side of the thigh;
    second anchor means for pivotally securing the lower ends of the rod assemblies to the patient's lower leg adjacent the ankle;
    means for locking the pivot joints of the rod assemblies in a selected pivotal position with respect to one another; and
    length adjustment means on each rod assembly for adjusting the length of the rod assemblies so that the position of the pivotal joint with respect to the knee is selectively adjustable as the knee straightens said length adjustment means including means on said second anchor means for slidably receiving the lower ends of the rod assemblies and means for locking said lower ends in a selected position within the receiving means.

2. The device of claim 1 wherein said receiving means includes a hollow tube pivotally secured to the second anchor means.

3. The device of claim 1 wherein each rod assembly includes upper and lower rod sections each having upper and lower ends, the lower end of the upper rod section being pivotally secured to the upper end of the lower rod section so as to define the pivotal joint of the rod assemblies.

4. The device of claim 3 wherein the lower end of the upper rod and the upper end of the lower rod each have an enlarged disk with a serrated perimeter for mating engagement therebetween.

5. The device of claim 4 wherein the means for locking the pivot joints in a selected pivotal position includes a screw extending through one of the disks and threadably engaging a threaded aperture in the other of the disks, whereby tight-ening of the screw causes the serrations of the disks to matingly engage one another and thereby lock the rods against pivotal movement with respect to one another.

6. The device of claim 3 wherein the lower rod sections are shaped to follow the contours of the patient's calf.

7. The device of claim 1 further including tensioning means secured to the rod assemblies adjacent the pivotal joint thereof and extending at least partially around the patient's leg adjacent the knee so as to stretch the patient's knee and attached ligaments and muscles.

8. The device of claim 3 wherein the upper and lower rod section are initially arranged at an obtuse angle corresponding substantially to the contraction of the knee, and the angle is periodically increased until the patient's leg is straightened.

9. The device of claim 1 wherein the second anchor means comprises a foot splint, the splint including a foot portion and a leg portion, the foot and leg portion being integrally formed at substantially right angles to one another.

10. A method of straightening a contracted knee of a patient, comprising:
    securing a leg brace onto the patient's leg, the brace including a first anchoring means attached to the patient's thigh, a second anchoring means attached to the patient's lower leg, and a pair of elongated rod assemblies positioned on opposite sides of the patient's knee, the rod assemblies each having an upper rod section with an upper end pivotally connected to the first anchoring means, and a lower rod section with a lower end pivotally connected to the second anchoring means, each rod assembly having a pivotal joint interconnecting the upper and lower rod sections, and each rod assembly having an adjustable length;

adjusting the length of the rod assemblies so that the pivotal joint of the assemblies are aligned with a patient's knee;

locking the joints of the rod assemblies so as to define an obtuse angle between the upper and lower rod sections of the rod assemblies, the angle being greater than the angle of contraction of the patient's knee; securing straps to the rod assemblies adjacent the joint thereof and around the patient's leg adjacent the knee so as to exert a stretching pressure on the knee and attached ligaments and muscles;

maintaining the stretching pressure on the knee and attached ligaments and muscles, so as to stretch the knee and thereby reduce the extent of knee contracture; and periodically increasing the angle between the upper and lower rod section of the rod assemblies so as to further stretch the knee until contracture of the knee is eliminated re-adjusting the length of the rod assemblies each time the angle between the rod sections is changed so that the pivotal joint remains aligned with the patent's knee.

* * * * *